US011409091B2

(12) United States Patent
You et al.

(10) Patent No.: US 11,409,091 B2
(45) Date of Patent: Aug. 9, 2022

(54) METHOD OF OPERATING A SURGICAL MICROSCOPE AND SURGICAL MICROSCOPE

(71) Applicant: Carl Zeiss Meditec AG, Jena (DE)

(72) Inventors: Fang You, Aalen (DE); David Dobbelstein, Ulm (DE); Stefan Saur, Aalen (DE)

(73) Assignee: Carl Zeiss Meditec AG, Jena (DE)

(*) Notice: Subject to any disclaimer, the term of this patent is extended or adjusted under 35 U.S.C. 154(b) by 410 days.

(21) Appl. No.: 16/732,162

(22) Filed: Dec. 31, 2019

(65) Prior Publication Data

US 2021/0199940 A1  Jul. 1, 2021

(51) Int. Cl.
*G02B 21/00* (2006.01)
*G02B 21/02* (2006.01)
*G06F 3/01* (2006.01)
*A61B 90/00* (2016.01)
*G02B 27/01* (2006.01)

(52) U.S. Cl.
CPC ........ *G02B 21/0012* (2013.01); *A61B 90/361* (2016.02); *G02B 21/025* (2013.01); *G06F 3/012* (2013.01); *G06F 3/013* (2013.01); *G02B 2027/014* (2013.01); *G02B 2027/0138* (2013.01)

(58) Field of Classification Search
CPC .... A61B 2017/00216; A61B 2090/371; A61B 2090/372; A61B 2090/502; A61B 90/20; A61B 90/25; A61B 90/361; G02B 2027/0138; G02B 2027/014; G02B 2027/0187; G02B 21/0012; G02B 21/025; G06F 3/012; G06F 3/013
See application file for complete search history.

(56) References Cited

U.S. PATENT DOCUMENTS

| 5,641,288 A * | 6/1997 | Zaenglein, Jr. ........ F41G 3/2633 434/21 |
| 5,825,982 A | 10/1998 | Wright et al. |
| 6,459,926 B1 * | 10/2002 | Nowlin .................. A61B 34/30 600/102 |
| 7,190,513 B2 | 3/2007 | Obrebski et al. |
| 2006/0028400 A1 * | 2/2006 | Lapstun ............. G02B 27/0093 345/8 |

(Continued)

FOREIGN PATENT DOCUMENTS

| WO | 2015151447 A1 | 10/2015 |
| WO | 2018078470 A1 | 5/2018 |

OTHER PUBLICATIONS

U.S. Appl. No. 16/732,126, filed Dec. 31, 2019, Fang You et al., Carl Zeiss Meditec AG.

(Continued)

*Primary Examiner* — Dmitriy Bolotin
(74) *Attorney, Agent, or Firm* — Falk Ewers; Ewers IP Law PLLC (57) ABSTRACT

A method of operating a surgical microscope includes detecting a direction of gaze of a user and detecting an amount of a movement of a head of the user. The movement of the head of the user is of a translatory movement type and a rotatory movement type. Amounts of movements or rotations of the camera or changes in the magnification are performed based on the detected amount of a movement of the head of the user.

12 Claims, 4 Drawing Sheets

(56) References Cited

U.S. PATENT DOCUMENTS

| | | | |
|---|---|---|---|
| 2012/0307027 A1* | 12/2012 | Popovic | G06T 7/246 901/46 |
| 2013/0063580 A1* | 3/2013 | Ogawa | A61B 34/74 348/65 |
| 2014/0163359 A1* | 6/2014 | Sholev | A61B 1/00149 600/407 |
| 2014/0275760 A1* | 9/2014 | Lee | G16H 40/63 600/102 |
| 2014/0303643 A1* | 10/2014 | Ha | A61B 34/30 606/130 |
| 2016/0170488 A1* | 6/2016 | Hanamoto | G06T 3/40 345/156 |
| 2016/0225192 A1* | 8/2016 | Jones | G06F 3/017 |
| 2017/0059871 A1* | 3/2017 | Hashiba | A63F 13/24 |
| 2017/0068081 A1 | 3/2017 | Hirayama | |
| 2017/0115736 A1* | 4/2017 | Patel | G06F 3/013 |
| 2017/0143442 A1* | 5/2017 | Tesar | H04N 13/344 |
| 2018/0204380 A1* | 7/2018 | Kumar | G06F 3/0346 |
| 2018/0232050 A1* | 8/2018 | Ofek | G02B 27/017 |
| 2018/0356880 A1* | 12/2018 | Kashihara | G06F 3/0346 |
| 2019/0008595 A1 | 1/2019 | Popovic et al. | |
| 2019/0029765 A1* | 1/2019 | Crawford | A61B 90/361 |
| 2019/0294103 A1 | 9/2019 | Hauger et al. | |
| 2019/0327394 A1* | 10/2019 | Ramirez Luna | H04N 13/106 |
| 2019/0353457 A1* | 11/2019 | Northrup | G01S 5/16 |
| 2021/0186624 A1* | 6/2021 | Charles | A61B 5/1114 |
| 2021/0196396 A1* | 7/2021 | You | A61B 90/25 |
| 2021/0199940 A1* | 7/2021 | You | G02B 21/0012 |
| 2021/0349303 A1* | 11/2021 | Koch | G02B 21/368 |
| 2022/0035155 A1* | 2/2022 | Williams | G02B 27/017 |

OTHER PUBLICATIONS

U.S. Appl. No. 16/732,195, filed Dec. 31, 2019, Fang You et al., Carl Zeiss Meditec AG.

U.S. Appl. No. 16/732,218, filed Dec. 31, 2019, Fang You et al., Carl Zeiss Meditec AG.

* cited by examiner

METHOD OF OPERATING A SURGICAL MICROSCOPE AND SURGICAL MICROSCOPE

CROSS REFERENCE TO RELATED APPLICATIONS

This application relates to U.S. patent applications Ser. Nos. 16/732,126, 16/732,195, and 16/732,218, filed on Dec. 31, 2019, the entire contents of which are incorporated herein by reference.

TECHNICAL FIELD

The present disclosure relates to surgical microscopes and methods of operating such surgical microscopes.

BACKGROUND

Conventional surgical microscopes include a microscope body including microscopy optics having two oculars. The microscope body is carried by a support having an articulating structure such that the microscopy optics can be positioned and repositioned relative to an object by translatory and rotatory movements. These movements are initiated by the user looking into the oculars by applying a force to the microscope body using his hands, for example. Such surgical microscopes require the user to permanently look into the oculars which is fatiguing and may create pain, for example, in the neck of the user. Moreover, the user requiring his hands for repositioning the microscope has to lay aside the currently used surgical tool to the effect that the flow of the surgery is interrupted.

Newer surgical microscopes include a camera for recording images of the object under surgery, and a display for displaying the recorded images to the user of the microscope. The user can perform the surgery assuming a convenient position of the head and watch the images on the display since looking into oculars is no longer required. Moreover, the support of these microscopes may include actuators for positioning the articulated joints of the support such that the camera is positioned with a desired orientation at a desired location in space. The desired location and orientation can be inputted into the surgical microscope by various means. For example, WO 2015/151447 A1 describes a surgical microscope in which the direction of gaze of the user and movements of the head of the user are detected to determine new positions of the camera. The actuators of the support are then operated to reposition the camera according to the detected direction of gaze and head movements.

The technologies described above offer significant advantages over the conventional surgical microscope having oculars. Still, it has been found that the process of positioning the camera could be improved.

SUMMARY

The present disclosure has been achieved by taking the above considerations into account, and it is an object of the present disclosure to provide a surgical microscope and a method of operating such a surgical microscope thereby improving the user experience in operations involving a repositioning of the camera.

According to an aspect of the present disclosure, a surgical microscope includes at least one camera, a support for the at least one camera, wherein the support includes at least one actuator for positioning the at least one camera relative to an object, and a display configured to display images recorded by the at least one camera.

According to an aspect of the disclosure, a method of operating the surgical microscope includes detecting a direction of gaze of a user, detecting an amount of a movement of a head of the user, wherein the movement of the head of the user is of a translatory movement type and a rotatory movement type, determining an amount of movement of the camera, and moving the camera by the determined amount of movement. The determined amount of movement of the camera may include an amount of rotatory movement of the camera and an amount of translatory movement of the camera.

According to an aspect of the disclosure, the amount of the rotatory movement of the camera is determined based on the detected amount of the movement of the head of the user, and the amount of the translatory movement of the camera is determined such that a location of the object which is imaged to a predetermined position within the displayed image when the moving of the camera has been completed is determined based on the detected direction of gaze.

The predetermined position within the displayed image can be, for example, the center of the displayed image, or any other suitable position.

According to an aspect of the disclosure, the method further includes detecting of a start command, wherein the moving of the camera by the determined amount of movement is performed only after the start command has been detected. The start command may include at least one of a voice command issued by the user, an operation of a button performed by the user, and a gesture of the user. The gesture of the user can be, for example, a gesture by the hand of the user or a gesture performed by a surgical tool operated by the user within the field of view of the at least one camera. For example, the user may initiate a process of positioning of the at least one camera relative to the object by issuing a voice command, such as "start".

The positioning of the camera includes a displacement of the field of view of the camera. For example, if a first location of the object is imaged to the center of the displayed image, the user may gaze at a position of the displayed image which is offset from the center of the displayed image. The location of the object imaged to this position offset from the center is then determined as the new location of the object which should be imaged to the center of the displayed image after the positioning of the at least one camera has been completed.

The positioning of the camera may further include a change of the orientation of the camera relative to the object if the user moves his head subsequent to the start command. The amount of the corresponding rotatory movement of the camera is determined based on the detected amount of movement of the head of the user.

The movement of the head of the user can be of two different types: a translatory movement and a rotatory movement.

According to an aspect of the disclosure, the amount of the rotatory movement of the camera is determined based on the detected amount of rotatory movement of the head of the user, while the determined amount of the rotatory movement of the camera is independent from the translatory movement of the head of the user.

According to another aspect of the disclosure, the amount of the rotatory movement of the camera is determined based on the detected amount of translatory movement of the head of the user, while the determined amount of the rotatory movement of the camera is independent from the rotatory movement of the head of the user.

According to further aspect of the disclosure, the amount of the rotatory movement of the camera is determined based on a combination of the detected amount of translatory movement of the head of the user and the detected the rotatory movement of the head of the user.

According to an aspect of the disclosure, the dependency of the determined amount of the rotatory movement of the camera from the detected amount of movement of the head of the user can be progressive. For example, the amount of the rotatory movement of the camera can be determined such that the determined amount of the rotatory movement is a first camera movement amount when the detected amount of the movement of the head of the user of a given type and in a given direction is a first head movement amount, and the determined amount of the rotatory movement can be a second camera movement amount when the detected amount of the movement of the head of the user of the given type in the given direction is a second head movement amount, wherein the second head movement amount is 1.1 times the first head movement amount, and wherein the second camera movement amount is larger than 1.2 times the first camera movement amount.

According to an aspect of the disclosure, the dependency of the determined amount of the rotatory movement of the camera from the detected amount of movement of the head of the user can be declining. For example, the amount of the rotatory movement of the camera can be determined such that the determined amount of the rotatory movement is a first camera movement amount when the detected amount of the movement of the head of the user of a given type and in a given direction is a first head movement amount, and the determined amount of the rotatory movement can be a second camera movement amount when the detected amount of the movement of the head of the user of the given type in the given direction is a second head movement amount, wherein the second head movement amount is 1.2 times the first head movement amount, and wherein the second camera movement amount is less than 1.1 times the first camera movement amount.

According to an aspect of the disclosure, the camera is a stereo camera configured to record a pair of stereo images. For example, the at least one camera may include two cameras for this purpose.

According to an aspect of the disclosure, the display is configured to display stereoscopic images. According to another aspect of the disclosure, the display is a head-mounted display which can be carried by the user of the surgical microscope. According to another aspect of the disclosure, the display includes a screen displaying the images obtained by processing the pair of stereo images, and a pair of glasses wearable by a user and allowing the user to see the displayed images obtained by processing left images of the pairs of stereo images with the left eye and to see the displayed images obtained by processing the right images of the pairs of stereo images with the right eye.

According to another aspect of the disclosure, the surgical microscope includes a controller configured to perform the methods illustrated above.

BRIEF DESCRIPTION OF THE DRAWINGS

The disclosure will now be described with reference to the drawings wherein.

DESCRIPTION OF EXEMPLARY EMBODIMENTS

The forgoing as well as other advantageous features of the disclosure will be more apparent from the following detailed description of exemplary embodiments with reference to the accompanying drawings. It is noted that not all possible embodiments necessarily exhibit each and every, or any, of the advantages identified herein.

In the exemplary embodiments described below, components that are alike in function and structure are designated as far as possible by alike reference numerals. Therefore, to understand the features of the individual components of a specific exemplary embodiment, the descriptions of other exemplary embodiments and of the summary of the disclosure should be referred to.

Figure 1:
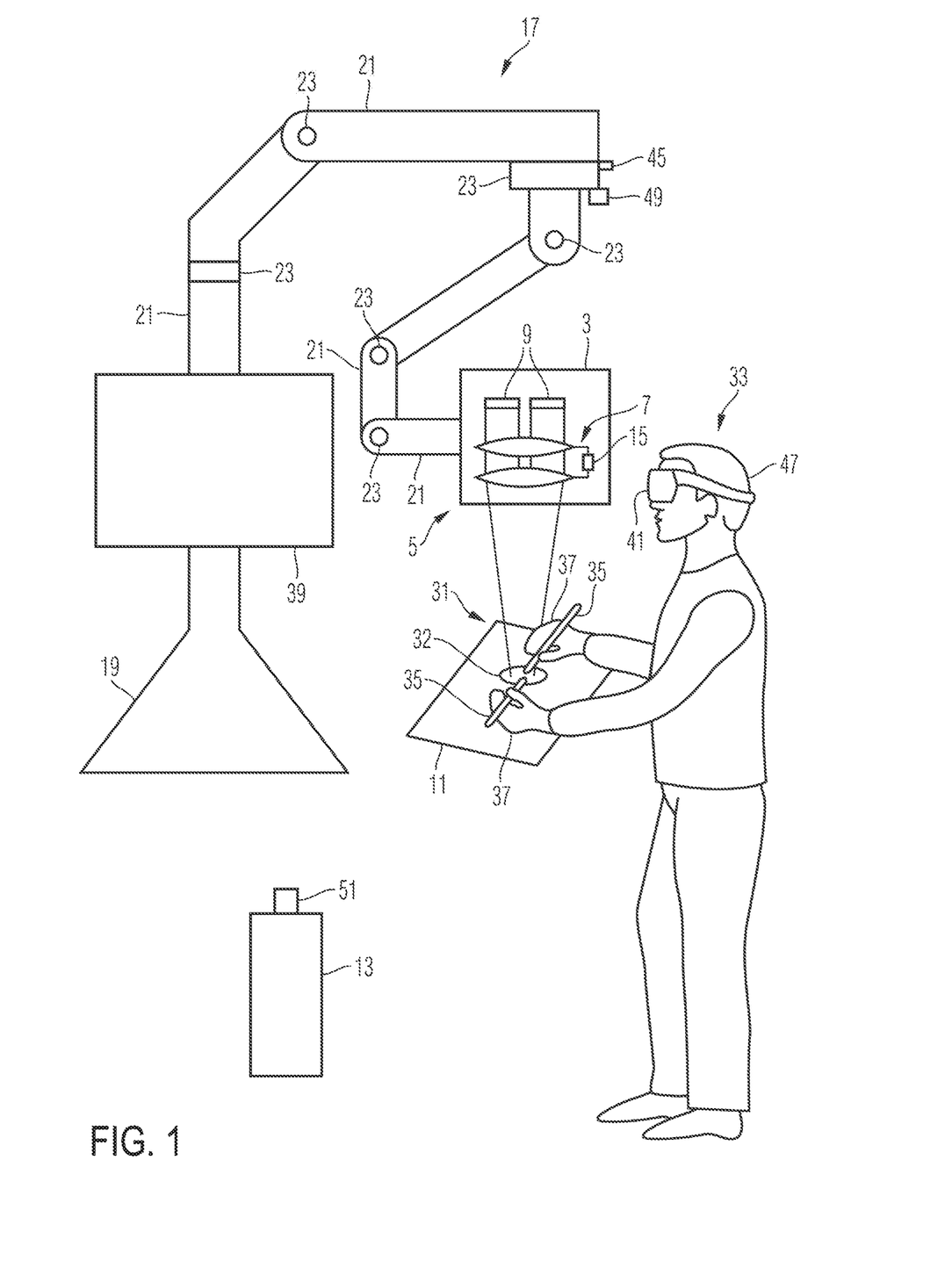
FIG. 1 shows a schematic illustration of a surgical microscope.

FIG. 1 is a schematic illustration of a surgical microscope 1. The surgical microscope 1 includes a microscope body 3, a housing, microscopy optics 5 including a magnifying zoom lens 7 and two cameras 9. The cameras 9 record images of a field of view of the cameras 9 in a focal plane 11. The optics 5 is configured to adjust a distance of the focal plane 11 from the microscope body by operating an actuator (not shown in FIG. 1) controlled by a controller 13 of the surgical microscope 1. Images of the field of view of the cameras 9 recorded by the cameras 9 are transmitted to the controller 13. The magnification of an object located in the field of view in the images recorded by the cameras 9 can be adjusted by the controller by operating an actuator 15 of the zoom lens 7.

The microscope body 3 is carried by a support 17 including a base 19 placed on a floor of an operation room, and plural members 21 connected by joints including actuators 23 controlled by the controller 13 in order to position the microscope body 3 within an accessible region of the operation room. The support 17 is configured to be controlled by the controller 13 such that the microscope body 3 performs both translatory movements in three independent directions and rotatory movements about three independent axes. Specifically, the actuators 23 of the support can be operated to position the cameras 9 such that the field of view of the cameras coincides with a surgical area 31 were a user 33 of the surgical microscope 1 performs a surgery with surgical tools 35 held by his hands 37. For this purpose, the user watches the surgical area 31 by looking at a display showing images transmitted from the controller 13. The images displayed on the display can be images obtained by processing the images recorded by the cameras 9. The processing of the images may include any image processing operation, such as cropping, rotating, contrast enhancement, color correction, and direct display of the recorded images without substantial changes to the image data.

The display can be, for example a flat panel display 39 which can be mounted on the support 17, or a head-mounted display 41 carried by the user 33.

The images recorded by the two cameras 9 are pairs of stereo images showing the surgical area from different angles. The pairs of stereo images can be watched by the user using the head-mounted display 41 so that the user 33 perceives a three-dimensional impression of the surgical area. Similarly, also the flat panel display 39 can be configured to display stereo images, wherein the user 33 will wear suitable glasses selecting the displayed images transmitted to the left and right eyes of the user. For example, the flat panel display 39 may alternatingly display the images for the left and right eyes while the glasses are active shutter glasses alternatingly transmitting light to the left and right eyes of the user 33. Moreover, the flat panel display 39 may display the images for the left and right eye of the user simultaneously using different polarization states of pixels of the screen, wherein the user 33 carries corresponding polarizing glasses.

The surgical microscope 1 further includes a sensor 45 allowing the controller to determine a position and orientation of a body portion, such as a head 47 of the user 33, relative to the microscope body 3, relative to the field of view 11 of the cameras 9 or relative to some other suitable position within the operation room. The sensor 45 can be mounted at any suitable position, such as an element of the support 17, on the display, 39 and 41. Moreover, the sensor may include plural sensor elements arranged at plural distributed locations.

The surgical microscope 1 further includes a sensor 49 allowing the controller 13 to determine a direction of gaze of the user 33. Specifically, the controller 13 may determine a position within the images displayed on the display 39 and 41 at which the eyes of the user are directed. Also, the sensor 49 can be mounted at any suitable position, such as an element of the support 17, on the display, 39 and 41. Moreover, the sensor may include plural sensor elements arranged at plural distributed locations.

The surgical microscope 1 further includes a sensor 51 allowing the controller 13 to receive commands issued by the user 33. For example, the sensor 51 may include a switch operated by the user 33 to enter a start command and a stop command. Moreover, the sensor 51 may include a microphone allowing the controller 13 to detect voice commands, such as "start" and "stop".

A method of positioning the cameras 9 relative to the object 32 will now be described with reference to the flow chart shown in FIG. 2. The method starts with a decision step 1 in which the controller determines whether a start command is detected. The start command may be the word "start" spoken by the user 33, for example.

If the start command is detected, the method continues with a step 103, in which the direction of gaze of the user is detected. Moreover, an initial position of the head of the user is detected in a step 105 which is performed subsequent to step 103 in the flowchart of FIG. 2. However, the direction of gaze can be detected subsequent to the detection of the initial position of the head 47 of the user 33, or the direction of gaze and the initial position of the head 47 of the user 33 can be detected simultaneously. Moreover, in the method illustrated above, the direction of gaze of the user is determined subsequent to the detection of the start command. However, it is also possible to permanently monitor the direction of gaze of the user in regular intervals and to use the most recent detected gaze direction for the purposes of the illustrated method upon receipt of the start command.

Figure 3A:
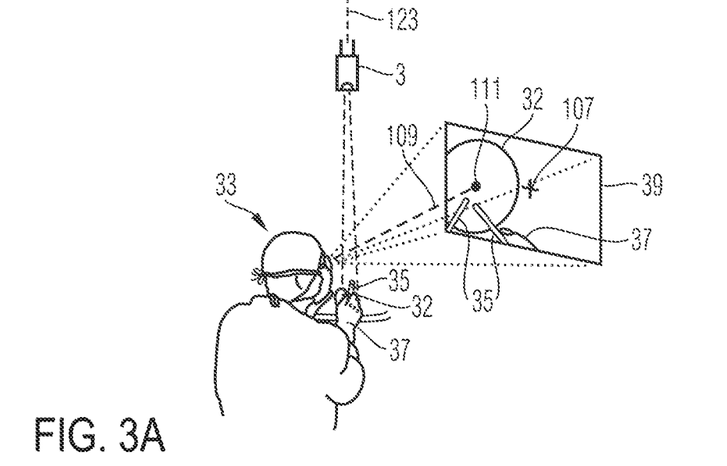
FIGS. 3A to 3C schematically illustrate situations occurring when performing the method shown FIG. 2.

The situation subsequent to the detection of the start command is illustrated in FIG. 3A. In this figure, the microscope body 3 including the cameras 9 is positioned relative to the object 33 such that the object 32, tools 35 and a portion of the hand 37 of the user are located within the field of view of the cameras 9. The corresponding images of the object 32, tools 35 and hand 37 as recorded by the cameras 9 are displayed on the display 39. The cameras 9 are oriented along an axis 123. As shown in FIG. 3A, the object 32, having a circular shape, is not completely positioned in the field of view of the camera. The center of the circular object 32 is displayed at a position of the display 39 which is offset relative to a center 107 of the display 39. It is assumed that the user 33 intends to position the cameras 9 relative to the object 32 such that the object 32 is centered relative to the display 39. For this purpose, the user 33 issues the start command, which is detected by the controller 13 and lets the controller 13 detect the direction of gaze of the user 33. The direction of gaze is indicated by a dotted line 109 in FIG. 3A which shows that the user gazes at a position 111 on the display 39, wherein the position 111 is offset relative to the center 107 of the display 39, and wherein the position 111 on the display 39 is a position onto which the center of the circular object 32 is imaged.

Subsequent to the detection of the direction of gaze in step 103, the method determines the location of the object 32 which is imaged to the position 111 of the display 39. Thereafter, a first amount of translatory movement of the cameras is determined. This first amount of translatory movement is determined such that the location of the object 32 onto which the user gazes is displayed at the center 107 of the display 39 when a translatory movement of the camera according to the first translatory movement amount has been completed.

Figure 3B:
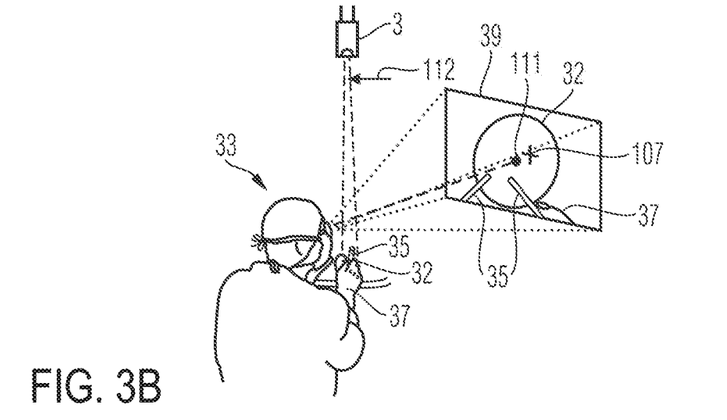

The translatory movement of the camera according to the determined translatory movement amount is performed in a step 113. The situation subsequent to step 113 is shown in FIG. 3B, in which the translatory movement according to the first amount of translatory movement is indicated by an arrow 112. In the situation shown in this figure, the cameras 13 have been moved such that the location 111 of the object 32 onto which the user 33 gazes is imaged to the center 107 of the display 39.

Thereafter, a decision step 114 is performed in which the controller determines whether a stop command is detected. The stop command may be the detected spoken word "stop", for example. If the stop command is detected, the method proceeds with a step 117 in which the current position of the head 47 of the user 33 is detected as the final position of the head of the user for the purposes of the illustrated method of positioning the surgical microscope.

In this illustration of the method, it is assumed that the user has turned his head 47 to the right by a certain amount between the detection of the start command in step 101 and the detection of the stop command in step 115. The difference between the rotatory position of the head in its final position and the rotatory position of the head in the initial position represents a detected amount of rotatory movement of the head of the user. An amount of rotatory movement of the cameras is determined based on the detected amount of rotatory movement of the head of the user, and a corresponding rotatory movement of the cameras is performed in a step 119.

Figure 3C:
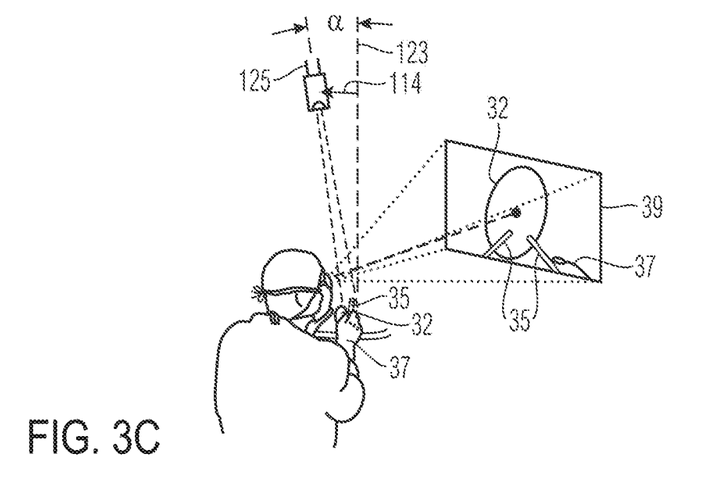

The rotatory movement of the camera performed in step 119 may result in a situation that the location 111 of the object 32 determined based on the direction of gaze of the user 33 is no longer imaged to the center 107 of the display 39. Therefore, a second amount of translatory movement is determined such that the location of the object determined based on the detected direction of gaze of the user is again imaged to the center 107 of the display. A translatory movement by the second translatory movement amount is performed in a step 121. This situation is shown in FIG. 3C. In FIG. 3C, the cameras are oriented along an axis 125 oriented at an angle α relative to the axis 123 of the cameras 9 in FIG. 3A. This angle α represents the determined amount of the rotatory movement of the camera. The rotatory movement of the camera results in a change of perspective of the images of the cameras displayed on the display 39. This change of perspective is apparent from FIG. 3C since the object 32 has an elliptical shape rather than the circular shape shown in FIG. 3A. An arrow 114 in FIG. 3C represents the second translatory movement amount.

Figure 2:
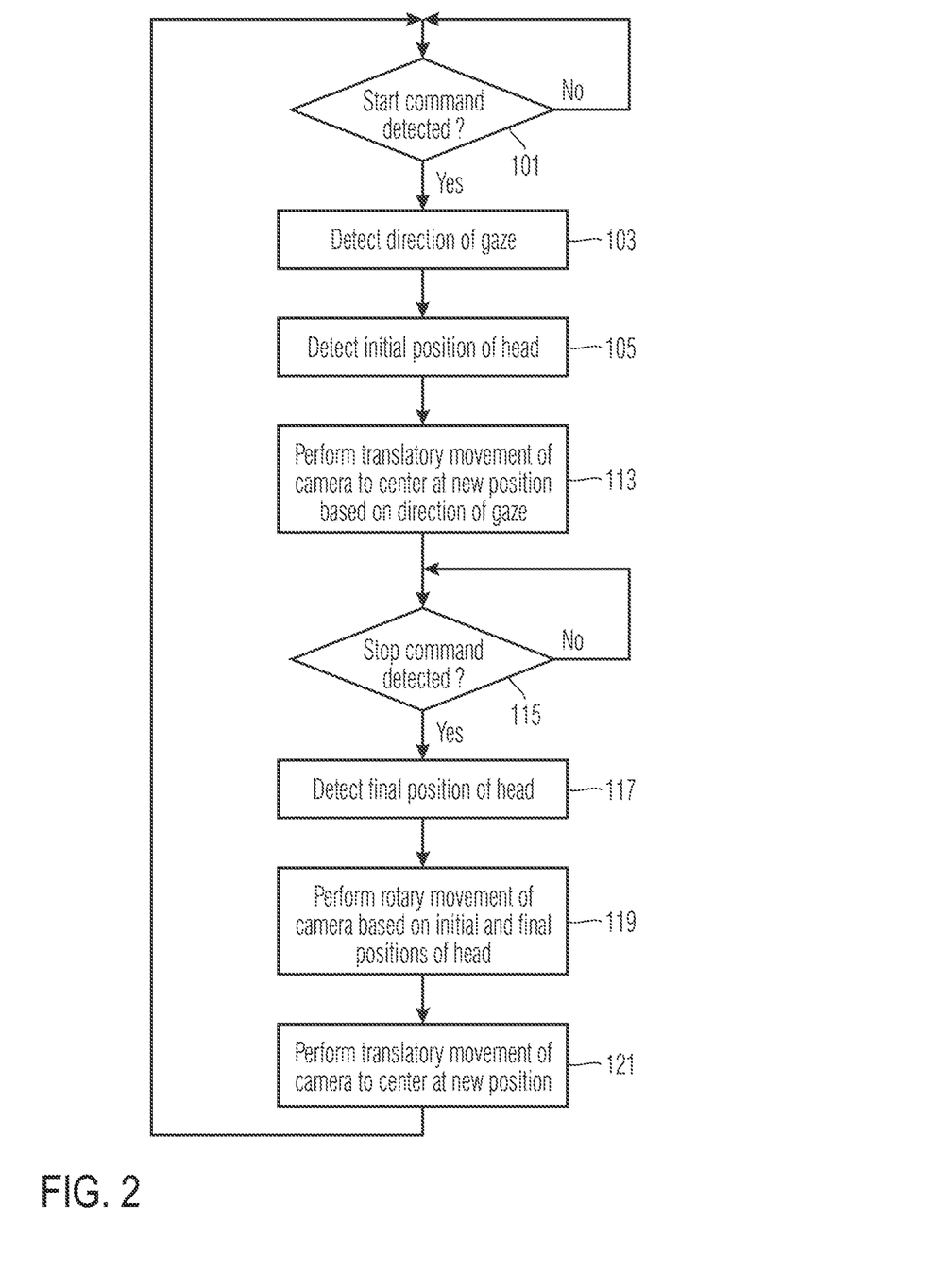
FIG. 2 shows a flow chart illustrating a method of positioning the cameras of the surgical microscope shown in FIG. 1 relative to the object.

The method illustrated in FIG. 2 allows the user to position the cameras relative to the object by performing controlled translatory and rotatory movements of the at least one camera.

In the method illustrated above with reference to FIGS. 2, 3A, 3B, and 3C, two first and second translatory movements of the cameras are performed in steps 113 and 121. It is, however, possible, to omit the first translatory movement of the camera of step 113 and to perform only one translatory movement of the camera in step 121 so that the intermediate situation shown in FIG. 3B is omitted. The single translatory movement will displace the cameras by an amount corresponding to the sum of the first and second translatory movement amounts illustrated above. Moreover, the rotatory movement and the translatory movement which are performed in subsequent steps 119 and 121 in FIG. 2, can be combined to one step which performs a simultaneous combined translatory and rotatory movement of the cameras between the situations shown in FIG. 3A and FIG. 3C.

Figure 4:
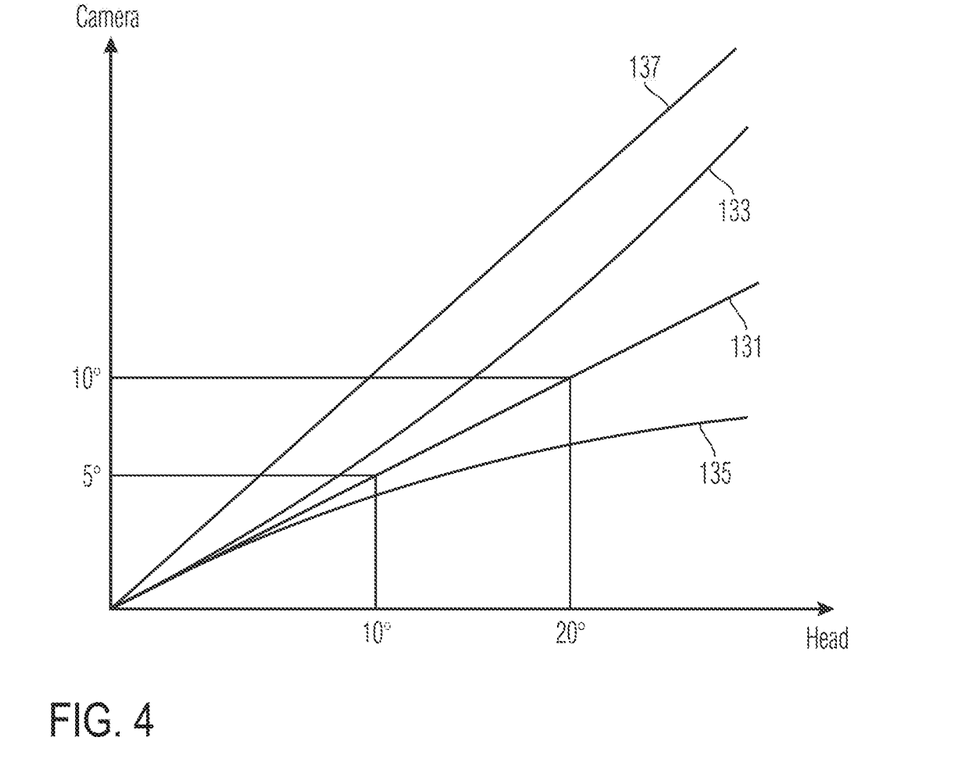
FIG. 4 shows graphs illustrating dependencies between detected movement amounts of the head of the user and rotatory movement amounts of the camera when performing the method shown in FIG. 2.

The determination of the amount of the rotatory movement of the cameras based on the detected rotatory amount of movement of the head of the user will be described with reference to FIG. 4. FIG. 4 shows graphs representing the rotatory movement of the camera in dependence of the detected rotatory movement of the head. The dependency between the rotatory movement of the head and the rotatory movement of the camera may have various dependencies. A line 131 represents an exemplary linear dependency. According to the linear dependency of line 131, a rotation of the head by 10° to the right results in a rotatory movement of the camera in a corresponding direction by 5°, and a rotation of the head to the right by 20° results in a rotatory movement of the cameras by 10°.

A line 133 shows a progressive dependency, in which the rotatory movement of the camera caused by a rotatory movement of the head by 20° is greater than 2.1 times the rotatory movement of the camera caused by a rotatory movement of the head by 10°. Similarly, a line 135 illustrates a declining dependency in which the rotatory movement of the camera caused by the rotatory movement of the head by 20° is less than 1.9 times the rotatory movement of the camera caused by the rotatory movement of the head by 10°.

The linear, progressive and declining dependencies may all have advantages in certain situations. Therefore, the dependency used by the controller 13 can be set by the user via a suitable interface. The dependencies 131, 133, and 135 describe the amounts of rotatory movements of the camera caused by rotations of the head of the user in the left-right direction. The left-right direction is the horizontal direction when the user holds his head upright. A line 137 in FIG. 4 represents the dependency of an amount of rotatory movement of the camera caused by a rotatory movement of the head of the user in the up-down direction. The up-down direction is the vertical direction when the user holds his head upright. Herein, line 137 shows a linear dependency. Progressive or declining dependencies can exist as well. Moreover, it is apparent from FIG. 4, that rotatory movements in the up-down direction result in greater amounts of rotatory movements of the cameras than equal amounts of rotatory movements of the head in the left-right direction. The different slopes of lines 137 and 131 are provided since the accessible range of head movements in the left-right direction is greater than in the up-down direction.

In the exemplary embodiment, the amount of the rotatory movement of the camera is determined based on the amount of rotatory movement of the head while the translatory movement of the head is ignored. However, it is also possible to perform the method described above such that the rotatory movement of the cameras is determined based on the detected translatory movement of the head while the rotatory movement of the head is ignored, or based on a combination of the detected translatory and rotatory movements of the head.

While the disclosure has been described with respect to certain exemplary embodiments thereof, it is evident that many alternatives, modifications and variations will be apparent to those skilled in the art. Accordingly, the exemplary embodiments of the disclosure set forth herein are intended to be illustrative and not limiting in any way. Various changes may be made without departing from the spirit and scope of the present disclosure as defined in the following claims.

What is claimed is:

1. A method of operating a surgical microscope, the surgical microscope including at least one camera having a zoom lens, a support for the at least one camera, the support including at least one actuator for positioning the at least one camera relative to an object, and a display configured to display images recorded by the at least one camera, the method comprising:
   detecting a direction of gaze of a user;
   detecting an amount of a movement of a head of the user, the movement of the head of the user being of a translatory movement type and a rotatory movement type;
   determining the amount of the movement of the at least one camera; and
   moving the at least one camera by the amount of the movement of the head of the user;
   wherein the amount of the movement of the at least one camera includes the amount of a rotatory movement of the at least one camera and the amount of a translatory movement of the at least one camera,
   wherein the amount of the rotatory movement of the at least one camera is determined based on the amount of the movement of the head of the user, and
   wherein the amount of the translatory movement of the at least one camera is determined such that a location of the object which is imaged to a predetermined position within a displayed image when the moving of the at least one camera has been completed is determined based on the direction of gaze.

2. The method of claim 1, wherein:
   the amount of the rotatory movement of the at least one camera is determined such that the amount of the rotatory movement is a first camera movement amount when the amount of the movement of the head of the user of a given type and in a given direction is a first head movement amount,
   the amount of the rotatory movement is a second camera movement amount when the amount of the movement of the head of the user of the given type in the given direction is a second head movement amount, the second head movement amount is 1.1 times the first head movement amount, and the second camera movement amount is larger than 1.2 times the first camera movement amount.

3. The method of claim 1, wherein:

the amount of the rotatory movement of the at least one camera is determined such that the amount of the rotatory movement is a first camera movement amount when the amount of the movement of the head of the user of a given type and in a given direction is a first head movement amount, the amount of the rotatory movement is a second camera movement amount when the amount of the movement of the head of the user of the given type in the given direction is a second head movement amount, the second head movement amount is 1.2 times the first head movement amount, and the second camera movement amount is less than 1.1 times the first camera movement amount.

4. The method of claim 1, wherein:

the movement of the head of the user includes the movement of the head of the user of a given type in a horizontal direction and the movement of the head of the user of the given type in a vertical direction, the amount of the rotatory movement of the at least one camera is determined such that the amount of the rotatory movement of the at least one camera in the horizontal direction is a first camera movement amount when the amount of the movement of the head of the user of the given type in the horizontal direction is a first head movement amount, the amount of the rotatory movement of the at least one camera in the vertical direction is a second camera movement amount when the amount of the movement of the head of the user of the given type in the vertical direction is a second head movement amount, the second head movement amount is equal to the first head movement amount, and the second camera movement amount is smaller than the first camera movement amount.

5. The method of claim 1, further comprising:

detecting a start command, and wherein the moving of the at least one camera by the amount of the movement is performed only after the start command has been detected.

6. The method of claim 5, wherein the start command includes at least one of a voice command issued by the user, an operation of a button performed by the user, and a gesture of the user.

7. The method of claim 1, wherein the at least one camera is a stereo camera.

8. The method of claim 1, wherein the at least one camera includes two cameras.

9. The method of claim 1, wherein the display is configured to display stereoscopic images.

10. The method of claim 9, wherein the display is a head-mounted display.

11. The method of claim 10, wherein the display comprises:

a screen displaying the images obtained by processing the images recorded by a first camera and a second camera of the at least one camera; and a pair of glasses wearable by the user and allowing the user to see displayed images obtained by processing the images recorded by the first camera with his or her left eye and to see the displayed images obtained by processing the images recorded by the second camera with his or her right eye.

12. The surgical microscope comprising:

the at least one camera having the zoom lens;

the support for the at least one camera, the support including the at least one actuator for positioning the at least one camera relative to the object;

the display configured to display the images recorded by the at least one camera; and a controller configured to perform the method of claim 1 with the surgical microscope.

* * * * *